(12) United States Patent
Browder et al.

(10) Patent No.: US 8,411,820 B1
(45) Date of Patent: *Apr. 2, 2013

(54) 3D X-RAY MICROSCOPY IMAGING SYSTEM

(75) Inventors: Mark K. Browder, Frisco, TX (US); J. Richard Wood, Grapevine, TX (US); William B. Shores, Cedar Hill, TX (US)

(73) Assignee: Lockheed Martin Corp., Bethesda, MD (US)

( * ) Notice: Subject to any disclaimer, the term of this patent is extended or adjusted under 35 U.S.C. 154(b) by 516 days.

This patent is subject to a terminal disclaimer.

(21) Appl. No.: 12/604,626

(22) Filed: Oct. 23, 2009

Related U.S. Application Data

(63) Continuation-in-part of application No. 12/541,539, filed on Aug. 14, 2009.

(60) Provisional application No. 61/107,924, filed on Oct. 23, 2008.

(51) Int. Cl.
G01N 23/20 (2006.01)
G01N 23/04 (2006.01)

(52) U.S. Cl. .......................... 378/87; 378/43; 378/86

(58) Field of Classification Search ............... 378/43, 378/86
See application file for complete search history.

(56) References Cited

U.S. PATENT DOCUMENTS

| 4,035,616 | A | 7/1977 | Piringer .................. 235/78 RC |
| 4,935,616 | A | 6/1990 | Scott ..................... 250/213 VT |
| 5,044,006 | A | 8/1991 | Cyrulnik .................... 378/145 |
| 5,206,592 | A | 4/1993 | Buess et al. ................ 324/307 |
| 5,592,083 | A | 1/1997 | Magnusson ................. 324/300 |
| 5,635,721 | A | 6/1997 | Bardi ....................... 250/492.3 |
| 5,642,393 | A | 6/1997 | Krug et al. ................... 378/57 |
| 5,696,577 | A | 12/1997 | Stettner et al. .............. 356/4.01 |
| 5,751,830 | A | 5/1998 | Hutchinson .................. 382/103 |
| 5,754,290 | A | 5/1998 | Rajic et al. ................... 356/328 |
| 5,760,403 | A | 6/1998 | Elabd ..................... 250/370.11 |
| 6,088,423 | A | 7/2000 | Krug et al. ................... 378/57 |
| 6,194,898 | B1 | 2/2001 | Magnuson et al. ........... 324/300 |
| 6,952,163 | B2 | 10/2005 | Huey et al. ................... 340/521 |

(Continued)

OTHER PUBLICATIONS

U.S. Appl. No. 12/604,548, entitled "X-Ray Radar", filed Oct. 23, 2009, in the name of the inventor J. Richard Wood.

(Continued)

Primary Examiner — Thomas R Artman

(74) Attorney, Agent, or Firm — Lee, Jorgensen, Pyle & Kewalramani, P.C.

(57) ABSTRACT

The present disclosure presents, in various aspects and embodiments, a 3D X-ray microscopy imaging technique. Some aspects are directed to various embodiments of an apparatus for use in such a technique, such as an X-ray microscopy imaging system. Other aspects are directed to various embodiments of a method for use in such a technique, like a method for generating an X-ray image that has a gray-scale response proportional to range. Some, though not all, aspects of the technique are computer-implemented, and so include encoded program storage media, programmed computing apparatuses, and computer-implemented methods.

50 Claims, 4 Drawing Sheets

U.S. PATENT DOCUMENTS

| | | | |
|---|---|---|---|
| 7,023,956 B2 | 4/2006 | Heaton et al. | 378/57 |
| 7,135,672 B2 | 11/2006 | Land | 250/221 |
| 7,142,109 B1 | 11/2006 | Frank | 340/539.26 |
| 7,231,017 B2 | 6/2007 | Gertsenshteyn | 378/87 |
| 7,317,390 B2 | 1/2008 | Huey et al. | 340/552 |
| 7,327,137 B1 | 2/2008 | Crowley | 324/300 |
| 7,368,292 B2 | 5/2008 | Hummel et al. | 436/171 |
| 7,385,549 B2 | 6/2008 | Lovberg et al. | 342/22 |
| 7,433,054 B1 | 10/2008 | Tischhauser et al. | 356/519 |
| 7,453,552 B1 | 11/2008 | Miesak | 356/4.01 |
| 2003/0144800 A1 | 7/2003 | Davis et al. | 702/22 |
| 2004/0165187 A1 | 8/2004 | Koo et al. | 356/445 |
| 2004/0257224 A1 | 12/2004 | Sajkowsky | 340/539.13 |
| 2005/0079386 A1 | 4/2005 | Brown, Jr. | 428/690 |
| 2005/0099292 A1 | 5/2005 | Sajkowsky | 340/539.13 |
| 2005/0104603 A1 | 5/2005 | Peschmann et al. | 324/637 |
| 2006/0022140 A1 | 2/2006 | Connelly et al. | 250/338.1 |
| 2006/0145812 A1 | 7/2006 | Sajkowsky | 340/5.81 |
| 2007/0008135 A1 | 1/2007 | Sajkowsky | 340/572.1 |
| 2007/0025512 A1 | 2/2007 | Gertsenshteyn | 378/86 |
| 2007/0211922 A1 | 9/2007 | Crowley et al. | 382/115 |
| 2008/0111545 A1 | 5/2008 | Crowley | 324/234 |
| 2008/0120430 A1 | 5/2008 | Redmond | 709/231 |

OTHER PUBLICATIONS

U.S. Appl. No. 12/541,539, entitled "X-Ray Explosive Imager", filed Aug. 14, 2009, in the name of the inventor J. Richard Wood.

U.S. Appl. No. 12/605,002 entitled "3D X-Ray Reflection Microscopy Imaging System", filed Oct. 23, 2009, in the name of J. Richard Wood.

M. R. Carter, et al., "A Microchannel Plate Intensified, Subnanosecond, X-ray Imaging Camera", 41 *Physica Scripta* 390-395 (1990), for its teachings regarding the design, construction, and operation of MCP assemblies.

3D X-RAY MICROSCOPY IMAGING SYSTEM

CROSS-REFERENCE TO RELATED APPLICATIONS

The priority of U.S. Provisional Application Ser. No. 61/107,924, entitled "X-Ray RADAR", filed Oct. 23, 2008, in the name of the inventor J. Richard Wood is hereby claimed under 35 U.S.C. §119(e). This application is also hereby incorporated by reference for all purposes as if set forth verbatim herein.

This is a continuation-in-part of U.S. application Ser. No. 12/541,539, entitled "X-Ray Explosive Imager", filed Aug. 14, 2009, in the name of the inventor J. Richard Wood. The earlier effective filing date of this application is hereby claimed under 35 U.S.C. §120 for all common subject matter. This application is also hereby incorporated by reference for all purposes as if set forth verbatim herein.

STATEMENT REGARDING FEDERALLY SPONSORED RESEARCH OR DEVELOPMENT

Not applicable.

BACKGROUND OF THE INVENTION

1. Field of the Invention

The present invention pertains to a three-dimensional ("3D") X-ray microscopy imaging system, and more particularly to a technique for enhancing the resolution of the same.

2. Description of the Related Art

This section of this document introduces various aspects of the art that may be related to various aspects of the present invention described and/or claimed below. It provides background information to facilitate a better understanding of the various aspects of the present invention. As the section's title implies, this is a discussion of "related" art. That such art is related in no way implies that it is also "prior" art. The related art may or may not be prior art. The discussion in this section of this document is to be read in this light, and not as admissions of prior art.

"Microscopy" may be considered to be the art of examining things under a microscope. The most familiar type of microscopy is "optical microscopy", which is frequently encountered in high school science classes. Optical microscopy illuminates a slide mounted specimen on a landing using visible light which may then be magnified and viewed. However, there are many kinds of microscopes, many of which operate under fundamentally different principles.

One alternative type of microscope is an "X-ray microscope", with which one practices "X-ray microscopy". An X-ray microscope generates X-rays that are then directed at and pass through a specimen under examination. Sometimes the generated X-rays cause "secondary" X-rays to "fluoresce" from the specimen. The X-rays emanating from the specimen are not visible to the naked eye, and so must be imaged. An X-ray microscope therefore includes a sensor for detecting the X-rays that have passed through the specimen and generating an image therefrom. Conventional approaches today generate a digital image, which may be considered to be an ordered set of data. This data may be stored electronically or rendered so that it may be perceptible to humans. Thus, it may be rendered for display on a screen or printing. The output of the sensor therefore is usually processed by an electronic apparatus of some sort that typically includes at least rudimentary processing capabilities.

A "freeze frame" method of looking at biological and chemical motion has been demonstrated using detectors including modulated microchannel plate images and fast scintillator materials. The method gated of X-ray fluorescent microchannel plates with a short modulating pulse. This required a very short time constant of modulation depth for the microchannel plate, and scintillator fluorescence response, which is limited to approximately 0.1 nanoseconds, which gives only about one tenth of a foot or 1.2" of transmission range "slice". This is inadequate range gating to improve contrast images of objects on the order of 1.2" or thinner. A calibration method for modulated microchannel plate X-ray imagers has been demonstrated by using high energy lasers to generate a short pulse of X-rays, but this was not used as part of the working imaging microscope. See M. R. Carter, et al., "A Microchannel Plate Intensified, Subnanosecond, X-ray Imaging Camera", 41 *Physica Scripta* 390-395 (1990)

The present invention is directed to resolving, or at least reducing, one or all of the problems mentioned above.

SUMMARY OF THE INVENTION

The present invention, in its various aspects and embodiments, is a 3D X-ray microscopy imaging technique.

In a first aspect, the invention includes an X-ray microscopy imaging system, comprising: an X-ray source capable of emitting a plurality of radio-frequency modulated X-rays toward a specimen; and a sensor. The sensor is capable of: imaging a plurality of X-rays emanating from the specimen subjected to the radio-frequency modulated X-rays; and radio-frequency modulating the image.

In a second aspect, the invention includes an X-ray microscopy imaging system, comprising: means for emitting a plurality of radio-frequency modulated X-rays toward a specimen; and means for: imaging a plurality of X-rays emanating from the specimen subjected to the radio-frequency modulated X-rays; and radio-frequency modulating the image.

In a third aspect, the invention includes a computer-implemented method, comprising generating an X-ray image that has a grayscale response proportional to range.

In a fourth aspect, the invention includes a program storage medium encoded with instructions that, when executed by a computing device, perform a computer-implemented method for generating an X-ray image that has a grayscale response proportional to range.

In a fifth aspect, the invention includes a computing apparatus, comprising: a processor; a bus system; a storage; and a software component residing in the storage that, when invoked by the processor over the bus system performs a computer-implemented method for generating an X-ray image that has a grayscale response proportional to range.

In a sixth aspect, the invention includes an apparatus, comprising: means for acquiring two temporally successive, radio frequency modulated, X-ray microscopy images; and means for generating an X-ray image that has a grayscale response proportional to range.

The above presents a simplified summary of the invention in order to provide a basic understanding of some aspects of the invention. This summary is not an exhaustive overview of the invention. It is not intended to identify key or critical elements of the invention or to delineate the scope of the invention. Its sole purpose is to present some concepts in a simplified form as a prelude to the more detailed description that is discussed later.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, the drawings illustrate specific embodiments herein described in detail by way of example. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

An X-ray transmission microscope with improved resolution is enabled by use of radio frequency modulation of the X-ray source, and radio frequency modulation of the imager which is detecting the magnified transmission λ-ray image from the scintillator material. This invention allows X-ray microscope images to be made that are only amplitude dependent within a given range resolution "slice" through the object, and thus in three dimensions. The image contrast is thus improved, as interfering X-ray shadows are "range gated" out of the image. By integrating the subsystems of radio frequency modulated microchannel plate imager with a similarly modulated X-ray source, a unique X-ray imaging microscope system is realized.

One or more specific embodiments of the present invention will be described below. The present invention is not limited to the embodiments and illustrations contained herein, but include modified forms of those embodiments including portions of the embodiments and combinations of elements of different embodiments as come within the scope of the appended claims. In the development of any such actual implementation, as in any engineering or design project, numerous implementation-specific decisions must be made to achieve the developers' specific goals, such as compliance with system-related and business related constraints, which may vary from one implementation to another. Moreover, such a development effort might be complex and time consuming, but would nevertheless be a routine undertaking of design, fabrication, and manufacture for those of ordinary skill having the benefit of this disclosure.

Furthermore, the phrase "capable of" as used herein is a recognition of the fact that some functions described for the various parts of the disclosed apparatus are performed only when the apparatus is powered and/or in operation. Those in the art having the benefit of this disclosure will appreciate that the embodiments illustrated herein include a number of electronic or electro-mechanical parts that, to operate, require electrical power. Even when provided with power, some functions described herein only occur when in operation. Thus, at times, some embodiments of the apparatus of the invention are "capable of" performing the recited functions even when they are not actually performing them—i.e., when there is no power or when they are powered but not in operation.

The present invention will now be described with reference to the attached figures. Various structures, systems and devices are schematically depicted in the drawings for purposes of explanation only and so as to not obscure the present invention with details that are well known to those skilled in the art. Nevertheless, the attached drawings are included to describe and explain illustrative examples of the present invention.

Figure 1A:
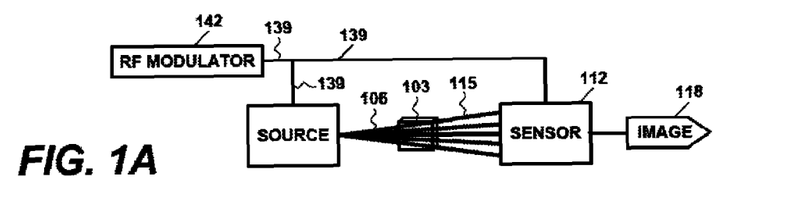
FIG. 1A conceptually depicts one particular embodiment of an X-ray microscopy imaging system constructed and operated in accordance with one aspect of the present invention.

FIG. 1A conceptually illustrates one particular embodiment of an X-ray microscopy imaging system 100. The system 100 is shown subjecting a target volume, or specimen, 103 to a plurality of X-rays 106 (only one indicated) generated and radio-frequency modulated as discussed further below. The system 100 comprises, in general, an X-ray source 109 and a sensor 112.

The X-ray source 109 is capable of emitting the plurality radio-frequency modulated X-rays 106 toward the target volume 103. The sensor 112 is capable of imaging a plurality of X-rays 115 (only one indicated) emanating from the target volume 103 and radio-frequency modulating the image. Radio frequency modulating the image impresses the image with a radio-frequency modulation. Upon imagining the X-rays 115, the sensor 112 then outputs the radio-frequency modulated image 118. The structure and operation of the X-ray source 109 and sensor 112 in the illustrated embodiment will now be discussed in further detail.

Figure 1B:
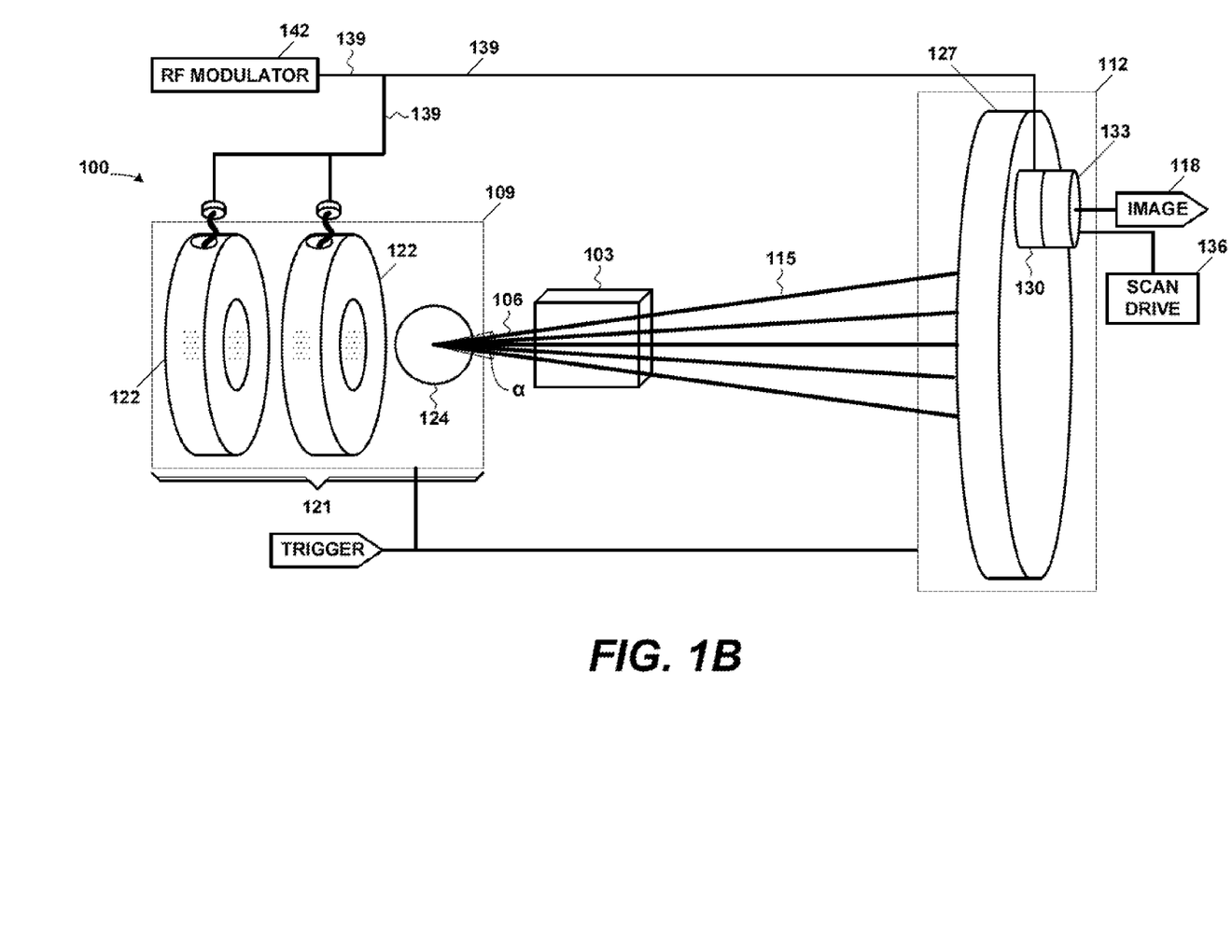
FIG. 1B conceptually illustrates one particular implementation of the X-ray microscopy imaging system of FIG. 1A.

Referring now to FIG. 1B, X-ray source 109 of the illustrated embodiment includes a radio-frequency modulated tube 121 comprising a pair of cavity resonator structures 122 that give rise to the magnetic or electric fields that deflect the electron beam and impart the intensity modulation of the electron beam at radio frequency with an electron beam dump 124. The radio-frequency modulated tube 121 is a high voltage, high energy tube. The radio-frequency modulated tube 121 may be, for example, a Klystron, such as is known in the art. Suitable implementations for the X-ray source 109 are commercially available off the shelf. For example, the NIR MCP-PMT and X-Ray Scintillator line of products offered by Hamamatsu Corp. offer several suitable alternatives. Hamamatsu Corp. can be reached in the United States at: 360 Foothill Rd, Bridgewater, N.J. 08807, ph: 908-231-0960; fax: 908-231-1218. Additional information can be obtained through those contacts or at www.hamamatsu.com over the World Wide Web of the Internet.

The sensor 112 of the illustrated embodiment comprises three parts. It includes a layer of a scintillating material 127 capable of intercepting the X-rays 115 emanating from the target volume 103 and fluorescing light (not shown) correlated thereto. A radio-frequency modulated microchannel plate 130 is located behind the scintillating material 127 to detect and amplify the fluoresced light. The microchannel plate 130 may also be referred to as a "phase plate". The amplification of the fluoresced light may also be described as "intensifying" the image, and so the microchannel plate 130 may be considered an "image intensifier". A detector array 133 is placed to detect the amplified fluorescent light output by the radio-frequency modulated microchannel plate 130. Again, suitable implementations are commercially available off the shelf, including the X-Ray Scintillator line of products offered by Hamamatsu Corp. mentioned above. Furthermore, information regarding imaging with such sensors and their fabrication is available from U.S. Pat. Nos. 6,531,225 and 6,762,420.

Figure 2:
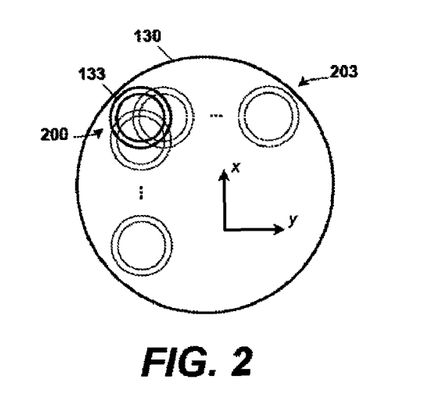
FIG. 2 illustrates the scanning of the detector array across the back of the microchannel plate in the sensor of the embodiment in FIG. 1B.

In the particular embodiment illustrated in FIG. 1B, the detector array 133 is not large enough to cover the entire back of the microchannel plate 130 simultaneously. The illustrated embodiment therefore includes a scan drive 136 that scans the detector array 133 from one position 200, shown in FIG. 2 in solid lines, to other positions 203 (only one indicated), shown in broken lines, across the back 131 of the microchannel plate 136. Such scan drives are known to the art and the scan drive 136 can be implemented using any suitable scan drive known to the art.

The illustrated embodiment also employs what is known as "range gating". In range gating, the output of the detector array 133 is used only during certain time periods when X-rays 115 of interest are expected to be received. These time periods typically are determined from trigger times and expected "time of flight" for the X-rays 115. Thus, the sensor 112 will need to know when the X-rays 115 are triggered. This can be accomplished by feeding the trigger signal 145 to the radio-frequency modulated tube 121 to the sensor 112 as well. The gating itself can be implemented by controlling power to the sensor 112 so that it is operational only at the desired times or by discarding the output of the sensor 112 during the "off" periods. Alternative embodiments may employ other gating techniques that may become apparent to those skilled in the art having the benefit of this disclosure.

The X-ray source 109 receives a modulation signal 139 from a radio-frequency ("RF") modulator 142. The modulation signal 139 is also input to the sensor 112. The radio frequency modulation of the directed energy tube 112, which can include modulation of amplitude, phase and/or frequency from a few kilohertz (e.g., 3 KHz) through 300 GHz, is applied across the two faces of the microchannel plate 130. Those in the art will recognize that, practically, the state of art in x-ray fluorescent imaging materials is at ~10 GHz, but "direct detection" of x-ray energy by new solid state detectors may very well have growth to 300 GHz. Typically, modulation will hold on one center frequency and amplitude/phase modulate, although some embodiments may modulate all three at once. This creates a biasing of the microchannel plate 130 that changes the recorded intensity of the image 118 as a function of range dependent phases of the transmitted radio frequency modulated X-ray energy.

In operation, the electron beam energy 145 within the radio frequency, radio-frequency modulated tube 121 generates the X-rays 106 when electrons (not shown) strike and decelerate into the beam dump 124 within the tube 121. The electron beam energy 145 is amplitude modulated, in this particular embodiment, with the radio frequency phase information of the modulation signal 139. This same amplitude modulation is imparted to the X-rays 106 generated from the electron beam dump 124.

The radio frequency amplitude modulated X-rays 106 propagating from the electron beam dump 124 within the radio-frequency modulated tube 121 have a preferred conical angle α, conceptually illustrated in FIG. 1B, of radiation from the tube volume toward the desired target volume 103 to be examined. The expanding cone a of X-rays 106 from the virtual point source of the electron beam dump 124 within the radio-frequency modulated tube 121 provides a means of casting a magnified shadow of an object placed in the path between the X-ray source 109 and a scintillator material 127. The transmitted X-rays 115 through the target volume will also contain this radio frequency modulation, containing energy modified by the materials in the object to be X-ray imaged.

The transmitted X-rays 115 intercept the scintillation material 127 in front of the radio frequency modulated microchannel plate 130. The scintillation material 127 fluoresces across an optical frequency range that the microchannel plate 130 is designed to amplify. The scintillation material 127 has a time constant small enough that the amplitude of the fluorescence follows the radio frequency modulation rate. The resulting modulated microchannel plate light (not shown) is detected by the detector array 133 and recorded as the digital image 118.

The resulting amplitude image 118 is a set of ordered data that is a "grayscale" representation of the magnitude of the difference between the radio frequency phase bias on the microchannel plate 130 amplification response and the radio frequency modulated X-ray 106 intensity through the target volume 103. In practice, as series of images 118 are captured over time, each representing a sampling of the transmitted X-rays 115. The image 118 may be stored, rendered for human perception, processed for some further use, or any combination thereof.

For a given image 118, a subsequent frame of microchannel plate image data with a 90° phase difference between the transmitted X-ray and microchannel plate modulation is recorded. That is, between two successive images 118, there is a 90° phase difference between those quantities. The ratio of the two recorded images 118 creates a resulting image (not shown) that has a grayscale response proportional to range, rather than X-ray return amplitude. By taking the arctangent of the ratio of the two images 118, precise range-dependent grayscale increments can be resolved numerically. Note also that, by taking successive images 118, the target can be imaged in three dimensions.

Figure 3:
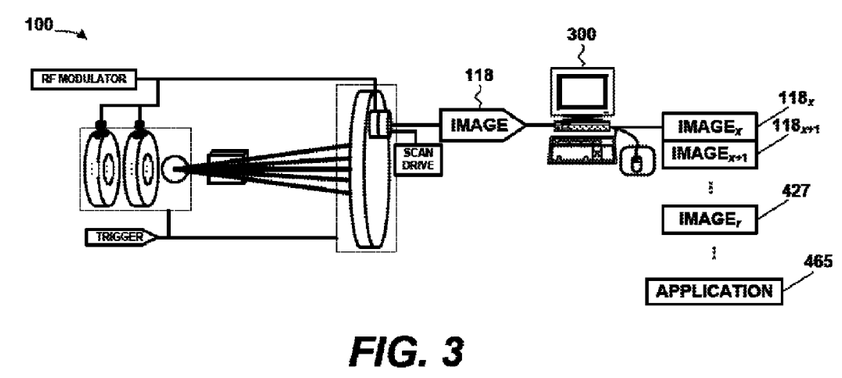
FIG. 3 depicts a second embodiment wherein the X-ray microscopy imaging system of FIG. 1B is deployed with a computing apparatus for image processing.

To that end, the X-ray microscopy imaging system 100 shown in FIG. 1B will typically be deployed in association with a computing apparatus 300, shown in FIG. 3. The computing apparatus 300 in the illustrated embodiment is a stand-alone work station. In alternative embodiments, the computing apparatus may be embedded in the apparatus 100 or may be part of a larger computing system. Instead of a workstation, the computing apparatus could be implemented in a desktop, laptop, notebook, etc., in other embodiments. The present invention admits wide variation in the implementation of the computing apparatus 300.

Figure 4:
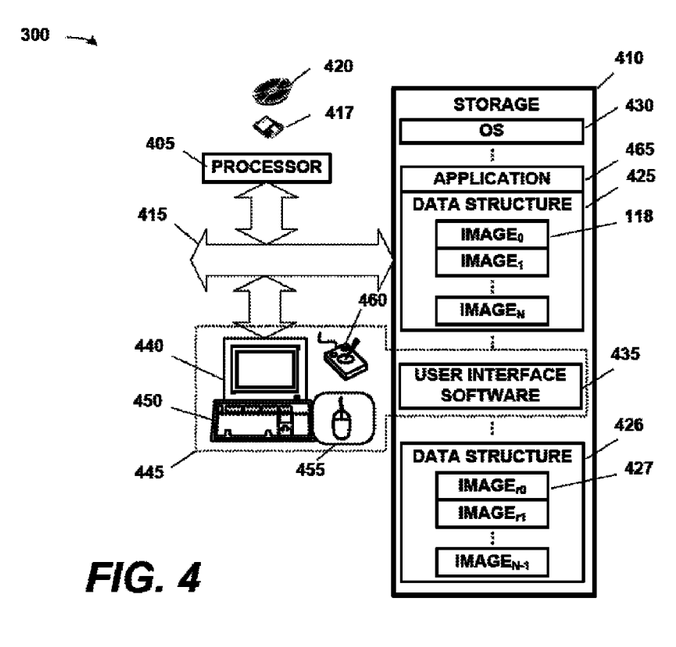
FIG. 4 shows selected portions of the hardware and software architecture of a computing apparatus such as may be employed in some aspects of the present invention.

In one aspect, the present invention is a software implemented method for generating an X-ray image that has a grayscale response proportional to range. FIG. 4 shows selected portions of the hardware and software architecture of the computing apparatus 300, first shown in FIG. 3, such as may be employed in some aspects of the present invention. The computing apparatus 300 includes a processor 405 communicating with storage 410 over a bus system 415.

The present invention admits wide variation in the implementation of the processor 405. Certain types of processors may be more desirable than others for some embodiments. For instance, a digital signal processor ("DSP") or graphics processor may be more desirable for the illustrated embodiment than will be a general purpose microprocessor. Other video handling capabilities might also be desirable. For instance, a Joint Photographic Experts Group ("JPEG") or other video compression capability and/or multi-media extension may be desirable. In some embodiments, the processor 405 may be implemented as a processor set, such as a microprocessor with a graphics co-processor, particularly for server architectures.

The storage 410 may be implemented in conventional fashion and may include a variety of types of storage, such as a hard disk and/or random access memory ("RAM") and/or removable storage such as a magnetic disk (not shown) or an optical disk (also not shown). The storage 410 will typically involve both read-only and writable memory. The storage 410 will typically be implemented in magnetic media (e.g., magnetic tape or magnetic disk), although other types of media may be employed in some embodiments (e.g., optical disk). The storage 410 may also employ various virtual memory and other memory management techniques. The present invention admits wide latitude in implementation of the storage 410 in various embodiments. In the illustrated embodiment, the storage 410 is internal memory implemented in a hard disk main memory, RAM, and in cache.

The bus system 415 will also vary widely by implementation. Depending upon the implementation, the bus system 415 may comprise an internal bus, a network backbone, or some combination thereof. For example, if the computing apparatus 300 is instead embedded with the X-ray microscopy imaging system 100, the bus system 415 may be implemented as an internal bus. On the other hand, if the computing apparatus 300 is but a part of a larger computing system across which the computing functionalities are distributed, then some type of external bus—i.e., a network backbone—will be employed. Either way, the bus system 415 may be implemented using conventional technologies.

The storage 410 is also encoded with an operating system ("OS") 430, user interface software 435, and an application 465. The user interface software 435, in conjunction with a display 440, implements a user interface 445. The user interface 445 may include peripheral input/output devices such as a keypad or keyboard 450, a mouse 455, or a joystick 460. The processor 405 runs under the control of the operating system 430, which may be practically any operating system known to the art. The application 465 may be invoked by the operating system 430 upon power up, reset, or both, depending on the implementation of the operating system 430. The application 465, when invoked, performs the method of the present invention. The user may also invoke the application 465 in conventional fashion through the user interface 445.

The storage 410 is also encoded with two data structures 425, 426. The data structure 425 contains the images 118 (only one indicated) that are acquired as described above. The data structure 426 contains the resultant images 427 (only one indicated) generated by the application 465 through the process generally described above. Thus, each resultant image 427 is an X-ray image that has a grayscale response proportional to range. The data structures 425, 426 may be implemented in any suitable type of data structure known to the art, such as a database, a list, or a queue. The data structures 425, 426 may be designed for long term storage of the images 118, 427 or to temporarily buffer them, depending on the implementation.

As mentioned above, the hardware and software architecture shown in FIG. 4 is exemplary only, and may find wide variation across numerous alternative embodiments. A good example of such variation is the implementation of the data structures 425, 426 described immediately above. Another good example is in the application 465. In other embodiments, the functionality residing in the application 465 may instead repose in some other kind of software component, such as a script, a daemon, etc.

There similarly may be variation in the situs of the various elements of the software aspects of the architecture. For example, there is no need for the images 118, 427 to reside on the same computing apparatus 300 or to reside on the same computing apparatus 300 as the application 465 by which they are processed and created. Some embodiments of the present invention may be implemented on a computing system, e.g., the computing system 500 in FIG. 5, comprising more than one computing apparatus. The computing system 500 employs a networked client/server architecture, but other architectures may be used.

Figure 5:
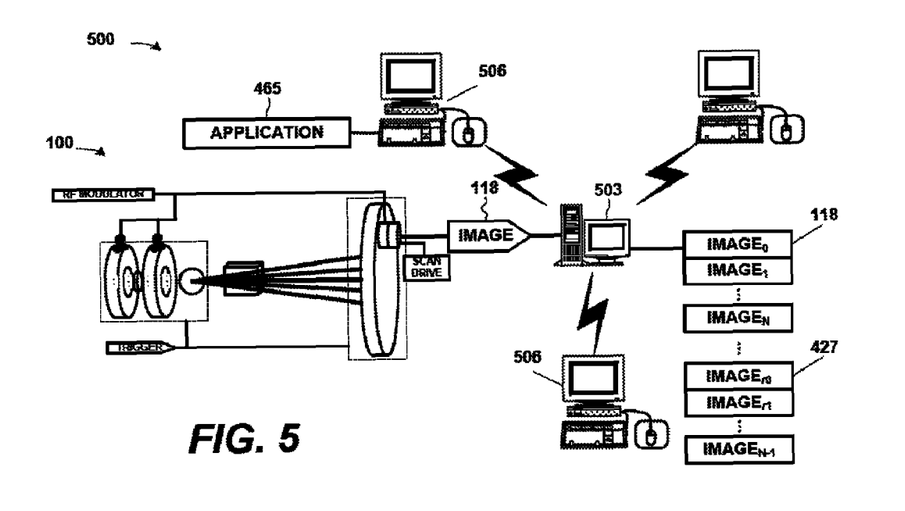
FIG. 5 illustrates a computing system on which some aspects of the present invention may be practiced in some embodiments.

In the embodiment of FIG. 5, the images 118, 427 (only one of each indicated) all reside in a data structure (not shown) residing on a server 503. The application 465 by which they are processed, however, resides on a workstation 506. Furthermore, although the images 118, 427 are all shown residing on the server 503, there is no requirement that they reside together. The images 118 might reside on the server 503 while the resultant images 427 might reside on the workstation 506. The invention admits wide variation in this respect.

Note that there is no requirement that the computing system 500 be networked. Alternative embodiments may employ, for instance, a peer-to-peer architecture or some hybrid of a peer-to-peer and client/server architecture. The size and geographic scope of the computing system 500 is not material to the practice of the invention. The size and scope may range anywhere from just a few machines of a Local Area Network ("LAN") located in the same room to many hundreds or thousands of machines globally distributed in an enterprise computing system.

Figure 6A:
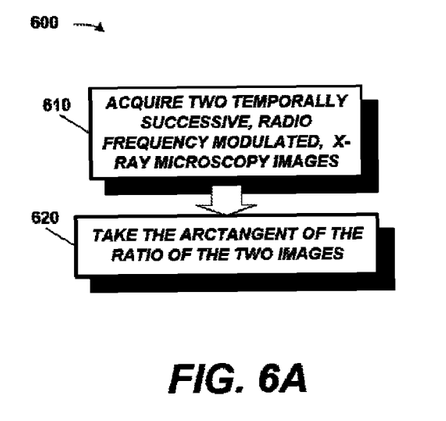
FIG. 6A illustrates a computer-implemented method for generating an X-ray image that has a grayscale response proportional to range.
Figure 6B:
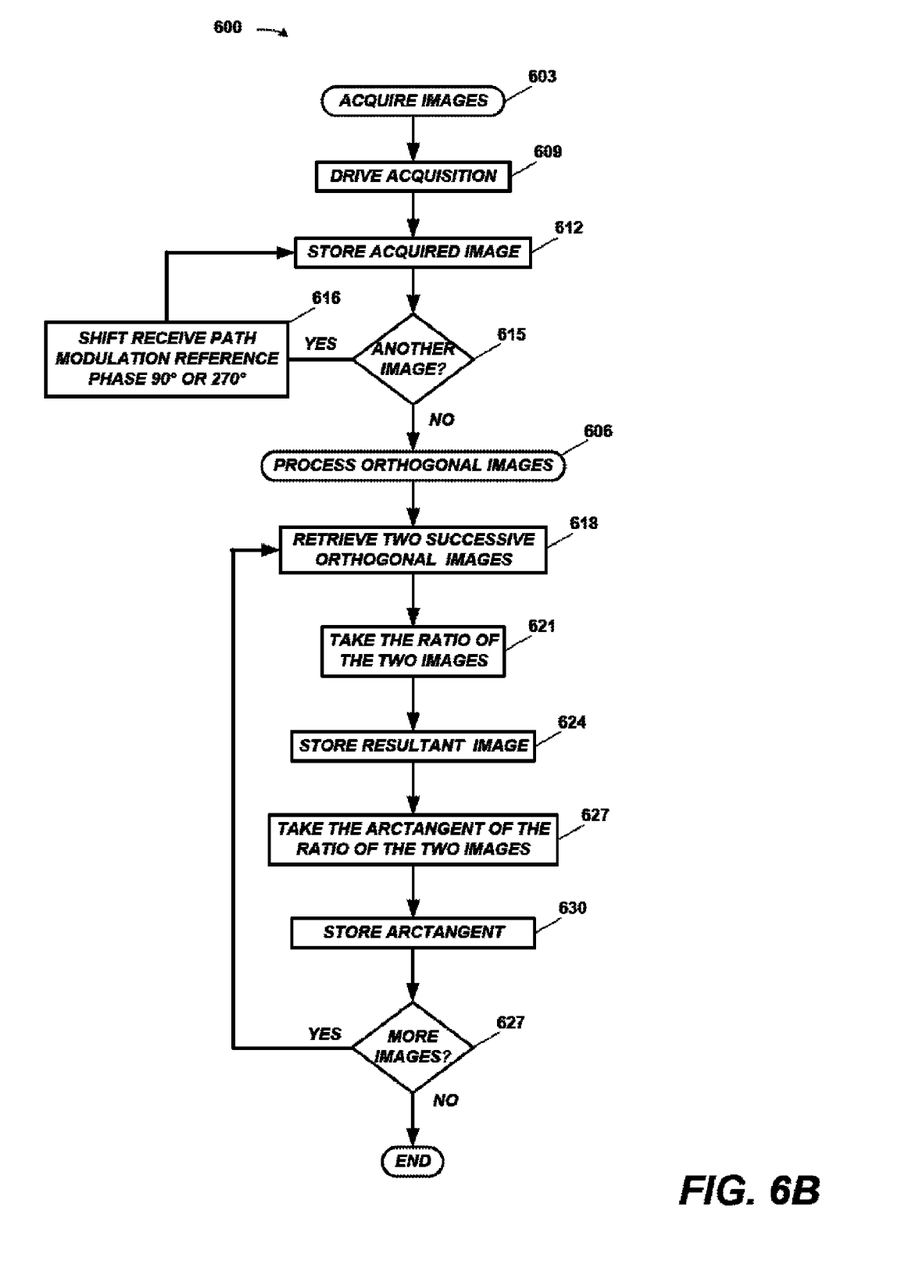
FIG. 6B is a flowchart of one particular embodiment of method for acquiring and processing X-ray microscopy images in accordance with one aspect of the invention.

Turning now to both FIG. 3 and FIG. 6B, in operation, the application 465 of the illustrated embodiment executes the process 600. The process 600 is performed in two parts—image acquisition (at 603) and image processing (at 606). In this particular embodiment, all acquisition occurs prior to processing. Alternative embodiments may "process on the fly", or process the images 118, shown in FIG. 1B, as they are acquired. The difference will create some differences in handling having both advantages and disadvantages relative to the illustrated embodiment. Those in the art having the benefit of this disclosure will appreciate not only these relative advantages and disadvantages, but also the differences in handling and will be able to implement such alternatives should they wish to do so.

The application 465 first drives (at 609) the acquisition of the images 118. Successive images will be orthogonal in the sense that they are taken with 90° shifts in receive path modulation between two successive images 118. This includes generating and transmitting the control signals for the X-ray trigger, the RF modulation, and the scanning and detection as described above. The images 118 are captured over time and stored (at 612). This continues until all the images 118 are captured and stored (at 615). Note that, after capturing any given image 118, the receive path modulation reference phase is shifted (at 616) 90° or 270° before storing (at 612) the next image 118.

Once acquisition (at 603) is finished, processing (at 606) begins. The application 465 processes the images 118 by first retrieving (at 618) two successive images 118. "Successive" in this instance means they follow one another in time at acquisition. As noted above, those two images 118 will exhibit a 90° phase difference between the transmitted X-ray and microchannel plate modulation. Consequently, the ratio of the two images 118 creates a resulting image 427 that has a grayscale response proportional to range, rather than X-ray return amplitude.

The application 465 takes the ratio (at 621) and stores (at 624) the resultant image 427. The application 465 then takes (at 627) the arctangent of the ratio of the two images 118 to numerically resolve precise range-dependent grayscale increments of the resultant image 427 and stores (at 630) them. The application does this for each of pair of images 118 (at 633) until there are no more pairs of images 118.

Thus, in one aspect, the invention includes a method 600, shown in FIG. 6A. The method 600 is a computer-implemented method for generating an X-ray image that has a grayscale response proportional to range. The method 600 comprises (at 610) acquiring two temporally successive, radio frequency modulated, X-ray microscopy images; and (at 620) taking the arctangent of the ratio of the two images.

Note, however, that the method 600 is but one particular embodiment by which the method of the invention may be practiced. For example, in alternative embodiments, an image can be taken without transmit or receive modulation, prior to or successive to the phase modulated images, to improve extraction of the phase information. Still other alternative embodiments may use two successive orthogonal phase modulated images, to be added together, or processed as "square root of the sum of the squares" of the intensities of the successive orthogonal phase images to establish a reference image level to improve extraction of phase information from intensity artifacts in the image. This can be done in place of the unmodulated image step in process just described immediately above in this paragraph, or in addition to the unmodulated image.

As is apparent from the discussion above, some portions of the detailed descriptions herein are consequently presented in terms of a software implemented process involving symbolic representations of operations on data bits within a memory in a computing system or a computing device. These descriptions and representations are the means used by those in the art to most effectively convey the substance of their work to others skilled in the art. The process is an electro-mechanical process. The process and operation require physical manipulations of physical quantities. Usually, though not necessarily, these quantities take the form of electrical, magnetic, or optical signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated or otherwise as may be apparent, throughout the present disclosure, these descriptions refer to the action and processes of an electronic device, that manipulates and transforms data represented as physical (electronic, magnetic, or optical) quantities within some electronic device's storage into other data similarly represented as physical quantities within the storage, or in transmission or display devices. Exemplary of the terms denoting such a description are, without limitation, the terms "processing," "computing," "calculating," "determining," "displaying," and the like.

Note also that the software implemented aspects of the invention are typically encoded on some form of program storage medium or implemented over some type of transmission medium. The program storage medium may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The invention is not limited by these aspects of any given implementation.

The following documents are hereby incorporated by reference for all purposes as if set forth verbatim and as modified by the teachings herein:

U.S. Provisional Application Ser. No. 61/107,924, entitled "X-Ray RADAR", filed Oct. 23, 2008, in the name of the inventor J. Richard Wood; and U.S. Provisional application Ser. No. 12/604,548, entitled "X-Ray RADAR", filed Oct. 23, 2009, in the name of the inventor J. Richard Wood;

U.S. application Ser. No. 12/541,539, entitled "X-Ray Explosive Imager", filed Aug. 14, 2009, in the name of the inventor J. Richard Wood.

U.S. Provisional Application Ser. No. 61/089,140, entitled "X-Ray Explosive Imager", and filed Aug. 15, 2008, in the name of the inventor J. Richard Wood, for all teachings and all purposes;

Japanese patent document JP 5-142396 for its teachings regarding X-ray telescopes;

U.S. Pat. No. 4,035,616, entitled, "Range Imaging Laser RADAR", issued Jun. 19, 1990, to The United States of America as assignee of the inventor Marion W. Scott, for its teachings regarding RF amplitude modulation using MCPs and range gating the receipt of backscatter;

U.S. Pat. No. 4,935,616, entitled "Range imaging laser radar", and issued Jun. 19, 1990, to The United States of America as represented by the Department of Energy as assignee of the inventor Marion W. Scott. M. R. Carter, et al., "A Microchannel Plate Intensified, Subnanosecond, X-ray Imaging Camera", 41 Physica Scripta 390-395 (1990), for its teachings regarding the design, construction, and operation of MCP assemblies; and U.S. Pat. No. 7,231,017, entitled "Lobster Eye X-ray Imaging System and Method of Fabrications Thereof", issued Jun. 12, 2007, to Physical Optics Corporation as assignee of the inventors Michael Gertsenshteyn, et al., in its entirety and for all of its teachings;

U.S. application Ser. No. 11/191,095, entitled "Lobster Eye X-ray Imaging System and Method of Fabrications Thereof", filed Jul. 27, 2005, in the name of the inventors Michael Gertsenshteyn, et al., and assigned to Physical Optics Corporation, and published as U.S. Patent Publication 2007/0025512 on Feb. 1, 2007, in its entirety and for all of its teachings;

U.S. Pat. No. 5,696,577, entitled "3D Imaging Underwater Laser Radar", issued Dec. 9, 1997, to Advanced Scientific Concepts, Inc. in the name of the inventors Roger Stettner and Howeard W. Bailey, for its teachings regarding range slicing.

This concludes the detailed description. The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. An X-ray microscopy imaging system, comprising:
   an X-ray source capable of emitting a plurality of radio-frequency modulated X-rays toward a specimen; and
   a sensor capable of:
      imaging a plurality of X-rays emanating from the specimen subjected to the radio-frequency modulated X-rays; and
      radio-frequency modulating the image.

2. The X-ray microscopy imaging, system of claim 1, wherein the X-ray source is capable of radio-frequency modulating any one or more of the amplitude of the generated X-rays, the phase of the generated X-rays, and the frequency of the generated X-rays.

3. The X-ray microscopy imaging system of claim 1, wherein the X-ray source is capable of radio-frequency modulating the generated X-rays at a frequency in to range from a few kilohertz through 300 GHz.

4. The X-ray microscopy imaging system of claim 1, wherein the sensor is range-gated.

5. The X-ray microscopy imaging system of claim 1, wherein the sensor includes:
   a layer of a scintillating material capable of intercepting the X-rays emanating, from the specimen and fluorescing light correlated thereto;
   a radio-frequency modulated microchannel plate behind the scintillating material to detect and amplify the fluoresced light; and
   a detector array for detecting, the amplified fluorescent light output by the radio-frequency modulated microchannel plate.

6. The X-ray microscopy imaging system of claim 5, wherein the sensor further includes a scanning mechanism scanning the radio-frequency modulated microchannel plate and the detector array across the scintillating material.

7. The X-ray microscopy imaging system of claim 1, further comprising a computing apparatus capable of processing the radio-frequency modulated images output by the sensor.

8. An X-ray microscopy imaging system, comprising:
   means for emitting, a plurality of radio-frequency modulated X-rays toward a specimen; and
   means for:
      imaging a plurality of X-rays emanating from the specimen subjected to the radio-frequency modulated X-rays; and
      radio-frequency modulating the image.

9. The X-ray microscopy imaging system of claim 8, wherein emitting means includes a radio-frequency modulated tube.

10. The X-ray microscopy imaging system of claim 8, wherein the emitting means includes means for radio-frequency modulating any one or more of the amplitude of the generated X-rays, the phase of the generated X-rays, and the frequency of the generated X-rays.

11. The X-ray microscopy imaging system of claim 8, wherein the emitting means includes means for radio-frequency modulating the generated X-rays at a frequency in a range from a few kilohertz through 300 GHz.

12. The X-ray microscopy imaging system of claim 8, wherein the imaging and modulating means is range-gated.

13. The X-ray microscopy imaging system of claim 8, wherein the imaging and modulating means includes:
   a layer of a scintillating material capable of intercepting the X-rays emanating from the specimen and fluorescing light correlated thereto;
   a radio-frequency modulated microchannel plate behind the scintillating material to detect and amplify the fluoresced light; and
   a detector array for detecting the amplified fluorescent light output by the radio-frequency modulated microchannel plate.

14. The X-ray microscopy imaging system of claim 8, further comprising a means for processing the radio-frequency modulated images output by the sensor.

15. The X-ray microscopy imaging system of claim 14, wherein the processing means comprises a computing apparatus.

16. A computer-implemented method, comprising generating an X-ray image that has a grayscale response proportional to range.

17. The method of claim 16, wherein generating the X-ray image includes:
   acquiring two temporally successive, radio frequency modulated, X-ray microscopy images; and
   taking the arctangent of the ratio of the two images.

18. The method of claim 17, wherein acquiring the two images includes:
   acquiring the first image;
   shifting the receive path modulation reference phase 90° or 270<; and
   acquiring the second image.

19. The method of claim 17, wherein taking the arctangent of the two images includes retrieving two successive images exhibiting a 90° phase difference between a transmitted X-ray and a microchannel plate modulation.

20. The method of claim 17, further comprising establishing a reference image.

21. The method of claim 20, wherein establishing a reference image inc hides taking an image without at least one of transmit or receive modulation.

22. The method of claim 20, wherein establishing a reference image includes adding two successive orthogonal phase modulated images.

23. The method of claim 20, wherein establishing a reference image includes processing, as a square root of the sum of the squares of the intensities of two successive orthogonal phase images.

24. A non-transitory program storage medium encoded with instructions that, when executed by a computing device, perform a computer-implemented method for generating an X-ray image that has a grayscale response proportional to range.

25. The non-transitory program storage medium of claim 24, wherein the method comprises:
   acquiring two temporally successive, radio frequency modulated, X-ray microscopy images; and
   taking the arctangent of the ratio of the two images.

26. The non-transitory program storage medium of claim 25, wherein acquiring the two images includes:

acquiring the first image;
shifting the receive path modulation reference phase 90° or 270°; and
acquiring the second image.

27. The non-transitory program storage medium of claim 25, wherein taking the arctangent of the two images includes retrieving two successive images exhibiting a 90° phase difference between a transmitted X-ray and a microchannel plate modulation.

28. The non-transitory program storage medium of claim 25, wherein the method further comprises establishing a reference image.

29. The non-transitory program storage medium of claim 28, wherein establishing a reference image includes taking an image without at least one of transmit or receive modulation.

30. The non-transitory program storage medium of claim 28, wherein establishing a reference image includes adding two successive orthogonal phase modulated images.

31. The non-transitory program storage medium of claim 28, wherein establishing a reference image includes processing as a square root of the sum of the squares of the intensities of two successive orthogonal phase images.

32. A computing apparatus, comprising:
   a processor;
   a bus system;
   a storage; and
   a software component residing in the storage that, when invoked by the processor over the bus system performs a computer-implemented method for generating an X-ray image that has a grayscale response proportional to range.

33. A computing apparatus, wherein the method comprises:
   acquiring two temporally successive, radio frequency modulated, X-ray microscopy images; and
   taking the arctangent of the ratio of the two images.

34. The computing apparatus of claim 33, wherein acquiring the two images includes:
   acquiring the first image;
   shifting the receive path modulation reference phase 90° or 270°; and
   acquiring the second image.

35. The computing apparatus of claim 33, wherein taking the arctangent of the two images includes retrieving two successive images exhibiting a 90° phase difference between a transmitted X-ray and a microchannel plate modulation.

36. The computing apparatus of claim 33, wherein the method further comprises establishing a reference image.

37. The computing apparatus of claim 36, wherein establishing a reference image includes taking an image without at least one of transmit or receive modulation.

38. The computing apparatus of claim 36, wherein establishing a reference image includes adding two successive orthogonal phase modulated images.

39. The computing apparatus of claim 36, wherein establishing a reference image includes processing as a square root of the sum of the squares of the intensities of two successive orthogonal phase images.

40. An apparatus, comprising:
   means for acquiring two temporally successive, radio frequency modulated, X-ray microscopy images; and
   means for generating an X-ray image that has a grayscale response proportional to range.

41. The apparatus of claim 40, wherein the acquiring means includes:
   an X-ray source capable of emitting, a plurality of radio-frequency modulated X-rays toward a specimen;
   a sensor capable of:
      imaging, a plurality of X-rays emanating from the specimen subjected to the radio-frequency modulated X-rays; and
      radio-frequency modulating the image.

42. The apparatus of claim 41, wherein the sensor includes:
   a layer of a scintillating material capable of intercepting the X-rays emanating from the specimen and fluorescing light correlated thereto;
   a radio-frequency modulated microchannel plate behind the scintillating material to detector and amplify the fluoresced light; and
   a detector array for detecting the amplified fluorescent light output by the radio-frequency modulated microchannel plate.

43. The apparatus of claim 40, wherein the generating means includes:
   a processor;
   a bus system;
   a storage; and
   a software component residing in the storage that, when invoked by the processor over the bus system performs a computer-implemented method for generating an X-ray image that has a grayscale response proportional to range.

44. The apparatus of claim 40, wherein acquiring the two images includes:
   acquiring the first image;
   shifting the receive path modulation reference phase 90° or 270°; and
   acquiring the second image.

45. The apparatus of claim 40, wherein generating the X-ray image includes taking the arctangent of the two successive orthogonal images.

46. The apparatus of claim 45, wherein taking the arctangent of the two successive orthogonal images includes retrieving two successive images exhibiting a 90° phase difference between a transmitted X-ray and a microchannel plate modulation.

47. The apparatus of claim 40, wherein the generating, means is further for establishing a reference image.

48. The method of claim 47, wherein establishing a reference image includes taking an image without at least one of transmit or receive modulation.

49. The method of claim 47, wherein establishing a reference image includes adding two successive orthogonal phase modulated images.

50. The method of claim 47, wherein establishing a reference image includes processing as a square root of the sum of the squares of the intensities of two successive orthogonal phase images.

* * * * *